US012414837B2

(12) United States Patent
Li (10) Patent No.: US 12,414,837 B2
(45) Date of Patent: Sep. 16, 2025

(54) NEEDLE CLAMPING DEVICE AND LEG SUPPORT DEVICE (71) Applicants: BEIJING HURWA ROBOT MEDICAL TECHNOLOGY CO., LTD., Beijing (CN); BEIJING HURWA ROBOT TECHNOLOGY CO., LTD., Beijing (CN)

(72) Inventor: Shugang Li, Beijing (CN)

(73) Assignees: Beijing Hurwa Robot Medical Tehnology Co., Ltd., Beijing (CN); Beijing Hurwa Robot Technology Co., Ltd., Beijing (CN)

( * ) Notice: Subject to any disclaimer, the term of this patent is extended or adjusted under 35 U.S.C. 154(b) by 540 days.

(21) Appl. No.: 17/709,232

(22) Filed: Mar. 30, 2022

(65) Prior Publication Data
US 2022/0218436 A1    Jul. 14, 2022

Related U.S. Application Data (63) Continuation of application No. PCT/CN2021/109000, filed on Jul. 28, 2021.

(30) Foreign Application Priority Data

Aug. 28, 2020 (CN) .......................... 202010885394.9
Oct. 16, 2020 (CN) .......................... 202022330951.9
Jan. 28, 2021 (CN) .......................... 202110120633.6

(51) Int. Cl.
A61B 90/57    (2016.01)
A61B 17/34    (2006.01)
(52) U.S. Cl.
CPC .......... *A61B 90/57* (2016.02); *A61B 17/3472* (2013.01); *A61B 2090/571* (2016.02)

(58) Field of Classification Search
CPC ................ A61B 90/57; A61B 17/3472; A61B 2090/571
See application file for complete search history.

(56) References Cited

U.S. PATENT DOCUMENTS 4,220,146 A * 9/1980 Cloutier ............. A61B 17/6425
606/90
5,167,223 A    12/1992 Koros et al.
(Continued)

FOREIGN PATENT DOCUMENTS

CN    2588947 Y    12/2003
CN    2659361 Y    12/2004
(Continued)

OTHER PUBLICATIONS

The first office action dated Feb. 8, 2022 for Chinese application No. 202010885394.9.
(Continued)

*Primary Examiner* — Erin McGrath (57) ABSTRACT

The present application discloses a needle clamping device and a leg support device. The needle clamping device includes a first component having a shaft portion; a second component hinged with the shaft portion, the second component includes a first portion and a second portion whose relative position is variable, the first portion and the second portion are arranged to clamp the shaft portion when the relative position changes; a clamping mechanism for clamping the needle, the clamping mechanism is connected to the second component, and the clamping mechanism is arranged so that at least part of the structure further clamps the first portion and the second portion, and drives the first portion and the second portion to change their relative position so that the second component clamps the shaft portion in the process of clamping the orthopaedic needle.

11 Claims, 7 Drawing Sheets

(56) References Cited

U.S. PATENT DOCUMENTS

| | | | | |
|---|---|---|---|---|
| 5,439,465 | A | * | 8/1995 | Tumibay ............ A61B 17/6408 606/105 |
| 5,792,046 | A | | 8/1998 | Dobrovolny |
| 5,921,985 | A | | 7/1999 | Ross, Jr. et al. |
| 6,074,401 | A | | 6/2000 | Gardiner et al. |
| 6,206,894 | B1 | | 3/2001 | Thompson et al. |
| 9,717,530 | B1 | * | 8/2017 | Ross ................. A61B 17/645 |
| 2003/0199738 | A1 | * | 10/2003 | Yager ................. A61B 90/57 600/227 |
| 2004/0144905 | A1 | | 7/2004 | Ropertz et al. |
| 2012/0150183 | A1 | * | 6/2012 | Dorawa ............ A61B 17/6466 606/59 |
| 2016/0278875 | A1 | | 9/2016 | Crawford |
| 2020/0008889 | A1 | | 1/2020 | Ho |

FOREIGN PATENT DOCUMENTS

| | | | |
|---|---|---|---|
| CN | 2744307 | Y | 12/2005 |
| CN | 101998842 | A | 3/2011 |
| CN | 203647498 | U | 6/2014 |
| CN | 205964137 | U | 2/2017 |
| CN | 108553255 | A | 9/2018 |
| CN | 109330813 | A | 2/2019 |
| CN | 109640862 | A | 4/2019 |
| CN | 109674612 | A | 4/2019 |
| CN | 109717938 | A | 5/2019 |
| CN | 111803199 | A | 10/2020 |
| CN | 111803200 | A | 10/2020 |
| CN | 111956441 | A | 11/2020 |
| CN | 213190924 | U | 5/2021 |
| CN | 213217541 | U | 5/2021 |
| CN | 213217542 | U | 5/2021 |
| EP | 0972491 | A1 | 1/2000 |
| EP | 3225224 | A1 | 10/2017 |
| EP | 3 409 231 | A1 | 12/2018 |
| GB | 559219 | A | 2/1944 |
| JP | H05208023 | A | 8/1993 |
| JP | 2011517998 | A | 6/2011 |
| JP | 2015065989 | A | 4/2015 |
| JP | 2015511501 | A | 4/2015 |
| WO | WO02083020 | A1 | 10/2002 |
| WO | 2018/102926 | A1 | 6/2018 |
| WO | 2018/220050 | A1 | 12/2018 |

OTHER PUBLICATIONS

International Search Report dated Oct. 26, 2021 for PCT application No. PCT/CN2021/109000.

The Extended European Search Report for European Patent Application No. 21765820.2, dated Jun. 7, 2022.

The Extended European Search Report dated Mar. 7, 2023 for European Application No. 21860031.0.

Notice of Refusal dated Feb. 14, 2023 for Japanese Patent Application No. 2022-525474.

The First Examination Opinion dated Aug. 2, 2022 for Chinese Application No. 202110120633.6.

* cited by examiner

NEEDLE CLAMPING DEVICE AND LEG SUPPORT DEVICE

CROSS-REFERENCE OF RELATED APPLICATIONS

The present application is a continuation of International Application No. PCT/CN2021/109000, filed on Jul. 28, 2021, which claims priority of the Chinese patent application 202010885394.9 filed on Aug. 28, 2020 and entitled "Needle Clamping Device and Fixing Device", the Chinese patent application 202022330951.9 filed on Oct. 16, 2020 and entitled "Leg Support Device" and the Chinese patent application 202110120633.6 filed on Jan. 28, 2021 and entitled "Leg Support Device", all of which are hereby incorporated by reference in their entireties.

TECHNICAL FIELD

The present application relates to the technical field of medical devices, in particular to a needle clamping device and a leg support device.

BACKGROUND

In scenarios such as knee arthroplasty, it is often necessary to keep the patient's limb fixed to facilitate the surgical operation. Taking knee arthroplasty as an example, at least the femur needs to be kept immobilized during the osteotomy of the femur. Traditional knee arthroplasty relies on an assistant to hold the patient's leg by hand to keep the leg fixed. The fixed way of holding the leg by hand increases the labor intensity of the assistant, and the accuracy and standardization depend on the physical strength level of the operator, and the stability is poor.

The fixed device can effectively reduce the physical exertion of the doctor and reduce the instability of manual operation. The fixing method of the fixing device may be to bind the affected limb to the support, or to establish a rigid connection with the bone of the affected limb through instruments such as threaded needles, and to fix the threaded needle on the support. However, the use of fixing devices increases the operation steps involved in the surgery, increases the duration of the surgery, and results in increased exposure time of the affected area. Especially in the fixing method of instruments using threaded needles, it is necessary to adjust the access of the threaded needle in multiple directions before implanting the threaded needle. After implanting, it is necessary to fix the threaded needle on the fixing device and lock the parts of the fixing device itself. The above operations are not conducive to reducing the complicated degree of surgery.

SUMMARY

The present application provides a needle clamping device and a leg support device so as to at least partially solve the above technical problems.

In a first aspect, the present application provides a needle clamping device for clamping an orthopedic needle, the needle clamping device comprises: a first component having a shaft portion; a second component hinged with the shaft portion, the second component includes a first portion and a second portion whose relative position is variable, the first portion and the second portion are arranged to clamp the shaft portion when the relative position changes; a clamping mechanism for clamping the needle, the clamping mechanism is connected to the second component, the clamping mechanism is arranged so that at least part of the structure further clamps the first portion and the second portion and drives the first portion and the second portion to change the relative position so that the second component clamps the shaft portion in the process of clamping the orthopaedic needle.

In a first possible implementation manner, the first portion and the second portion of the second component are a first clamping arm and a second clamping arm arranged side by side, a first end portion of the first clamping arm is connected to a first end portion of the second clamping arm, a predetermined distance is formed between a second end portion of the first clamping arm and a second end portion of the second clamping arm, and a shaft hole is formed between the first clamping arm and the second clamping arm; the second component is rotatably connected with the shaft portion of the first component through the shaft hole.

In combination with the above possible implementation manners, in a second possible implementation, the clamping mechanism includes: an inner shaft that penetrates through the second end portion of the first clamping arm and the second end portion of the second clamping arm, a first end and a second end of the inner shaft are distributed on both sides of the second component, and the first end is provided with a first limiting surface; a handle member movably arranged on the second end of the inner shaft, when the handle member is movable relative to the inner shaft, at least part of the structure can move in an axial direction of the inner shaft; a locking sleeve having a through hole, the locking sleeve is sleeved on the outside of the first end of the inner shaft, the locking sleeve can move relative to the inner shaft, the locking sleeve has a second limiting surfaces, the second limiting surface and the first limiting surface of the inner shaft are arranged face to face or diagonally opposite to each other; wherein, the second component forms limit for the handle member and the locking sleeve in the axial direction of the inner shaft.

In combination with the above possible implementation manners, in a third possible implementation manner, a first radial hole is provided on the first end of the inner shaft along the radial direction, a hole wall portion of the first radial hole facing away from an end surface of the first end is the first limiting surface, the locking sleeve is provided with a second radial hole along the radial direction, and a hole wall portion of the second radial hole that has the same direction as the end surface of the first end of the inner shaft is the second limiting surface. The first limiting surface is arranged diagonally opposite to the second limiting surface.

In combination with the above possible implementation manners, in a fourth possible implementation manner, the first end of the inner shaft is located in the locking sleeve, and the locking sleeve is provided with a limiting rod.

In combination with the above possible implementation manners, in a fifth possible implementation manner, the first end of the inner shaft is provided with a flange protruding radially, the flange is located on a side portion of an end of the locking sleeve facing away from the second component, a gap is formed between the flange and the end of the locking sleeve facing away from the second component, a side surface of the flange facing the locking sleeve is the first limiting surface, and an end surface of the first end facing the flange is the second limiting surface.

In combination with the above possible implementations, in a sixth possible implementation, the handle member includes a cylinder portion and a handle portion, the cylinder portion is connected with the handle portion, the handle portion radially protrudes out of the cylinder portion, the cylinder portion and the handle portion are sleeved outside the second end of the inner shaft and are threadedly connected with the second end of the inner shaft, an end of the handle portion is in contact with the second end portion of the first clamping arm. When the handle portion is rotated, it can drive the inner shaft to move the axial direction and drive the locking sleeve to squeeze the second end portion of the second clamping arm.

In combination with the above possible implementations, in a seventh possible implementation, the handle member is a cam handle, the cam handle includes a cam portion and a handle portion, the cam portion is connected with the handle portion, the cam portion is rotatably connected with the second end of the inner shaft. When the handle portion rotates to drive the cam portion to rotate, it can drive the inner shaft to move in the axial direction and drive the locking sleeve to squeeze the second end portion of the second clamping arm.

In combination with the above possible implementation manners, in an eighth possible implementation manner, the inner shaft is connected with the locking sleeve in ma manner of circumferential limit.

In combination with the above possible implementation manners, in a ninth possible implementation manner, an outer peripheral surface of the inner shaft at least includes a plane area parallel to the inner shaft, an inner peripheral surface of the through hole of the locking sleeve is provided with a matching surface matched with the plane area. The matching surface is fitted with the plane area to form the circumferential limit.

In combination with the above possible implementation manners, in a tenth possible implementation manner, an elastic member is further provided between the first end of the inner shaft and the locking sleeve, and the elastic member acts on the inner shaft and enables that the inner shaft have a tendency of protruding toward the outside of the sleeve.

In a second aspect, the present application provides a leg support device having the needle clamping device provided by any of the implementations of the first aspect. The leg support device includes: a base; a support rod assembly connected to the base; the needle clamping device is provided on the upper portion of the support rod assembly.

In a first possible implementation manner, the support rod includes a first support rod assembly and a second support rod assembly respectively disposed on two sides of the base, and at least one of the first support rod assembly and the second support rod assembly can be detachably connected to the base.

In combination with the above possible implementation manners, in a second possible implementation manner, the position of the support rod and the base relative to each other along a length direction of the side of the base is adjustable.

Compared with the prior art, embodiments of the present application have at least the following advantages:

In the needle clamping device provided in embodiments of the present application, the clamping structure in the needle clamping device can make the second component clamp the shaft portion of the first component while clamping the orthopaedic needle, or make the second component release the shaft portion of the first component while releasing the orthopaedic needle. The complicated degree of the operation in the process of locking and releasing orthopedic needles (such as threaded needles) is reduced, the operation is convenient, and time and effort are saved.

In addition, in the leg support device provided by the embodiment of the present application, at least one of the first support rod assembly and the second support rod assembly is detachably connected to the base respectively, and the needle clamping device mounted on the left or right can be selected according to the leg under surgery, which reduces the occupation of the surgery space and facilitates the operation around the knee joint of the human body. What more, the need for sterilization of instruments prior to surgery is reduced because only the support rod assembly that needs to be mounted on the base needs to be sterilized. In addition, the first support rod assembly and the second support rod assembly are located on both sides of the base, and the space between the two and the upper surface of the base can be used to lay the affected limb straight and flat to check the tension of the joint ligament during the surgery or after the surgery is completed, it is not necessary to remove the leg support device from the surgery table to make room for the affected limb to lay flat. Moreover, the leg is positioned by the first support rod assembly, which avoids the problems of poor stability and poor accuracy of the hand-holding fixation.

BRIEF DESCRIPTION OF THE DRAWINGS

The features, advantages and technical effects of the exemplary embodiments of the present application will be described below with reference to the accompanying drawings.

In the drawings, the drawings are not necessarily drawn according to actual scale.

DETAILED DESCRIPTION

Embodiments of the present application will be described in further detail below with reference to the accompanying drawings and examples. The following detailed description of the embodiments and the accompanying drawings are used to illustrate the principles of the present application by way of example, but should not be used to limit the scope of the present application, that is, the present application is not limited to the described embodiments.

In the description of this application, it should be noted that, unless otherwise specified, the meaning of "plurality" is two or more; The orientation or positional relationship indicated by the terms "upper", "lower", "left", "right", "inner", "outside" etc. is only for the convenience of describing the present application and simplifying the description, rather than indicating or implying that the indicated device or element must have a specific orientation, be constructed and operated in a specific orientation, and therefore should not be construed as restrictions to the present application. Furthermore, the terms "first", "second" etc. are used for descriptive purposes only and should not be construed to indicate or imply relative importance. "Vertical" is not strictly vertical, but within the allowable range of errors. "Parallel" is not strictly parallel, but within the allowable range of errors.

In the description of the present application, it should also be noted that, unless otherwise expressly specified and limited, the terms "install", "connect" and "connect" should be understood in a broad sense, for example, it may be a fixed connection, a detachable connection, or an integral connection; it can be direct connection or indirect connection through an intermediate medium. For those of ordinary skill in the art, the specific meanings of the above terms in the present application can be understood according to specific circumstances.

For a better understanding of the present application, embodiments of the present application are described below with reference to FIGS. 1 to 14.

Figure 1:
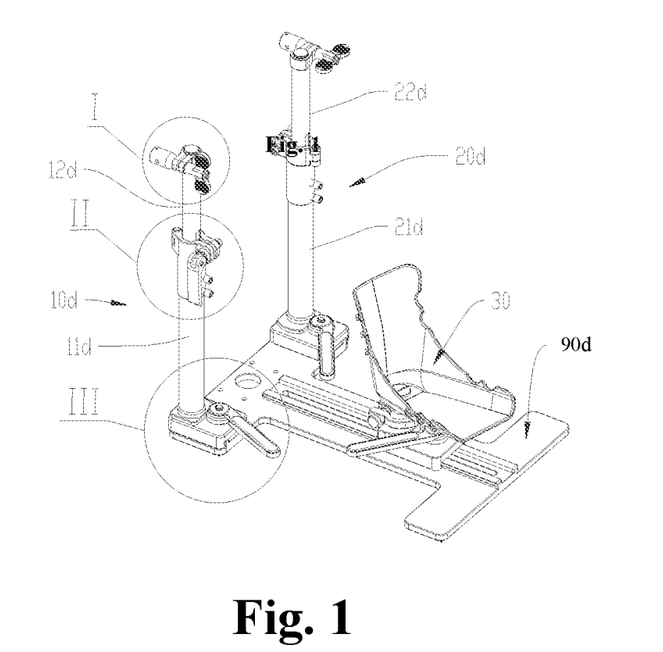
FIG. 1 is a structural schematic diagram of a leg support device according to an embodiment of the present application.

Referring to FIG. 1, FIG. 1 is a structural schematic diagram of a leg support device in an embodiment disclosed in the present application. The leg brace device can be used in surgical operations to support and fix an affected limb such as a leg, for example, to fix the femur in total knee arthroplasty.

In the first aspect, embodiments of the present application provide a leg support device, which includes: a base 90d, a first support rod assembly 10d, a second support rod assembly 20d, a first needle clamping device and a second needle clamping device. The structure of the first needle clamping device and the structure of the second needle clamping device can be the same.

The base 90d is used as the installation and support base of the device, and the first support rod assembly 10d and the second support rod assembly 20d are mounted on the base 90d.

Referring to FIG. 1, in some optional embodiments, the support bases of the two needle clamping devices are two independent support rod structures, namely a first support rod assembly 10d and a second support rod assembly 20d. The first support rod assembly 10d and the second support rod assembly 20d are detachably connected to the base 90d respectively, so that needle clamping device mounted on the left or right side can be selected according to the leg under operation. This can reduce the occupation of the surgical space and facilitate the operation around the knee joint of the human body. Also, the need for sterilization of instruments prior to surgery can be reduced, as only the support rod assembly that needs to be mounted on the base 90d needs to be sterilized.

There is no beam between the first support rod assembly 10d and the second support rod assembly 20d, so during or after the surgery, the doctor can directly lay the patient's leg flat for joint flexion and extension observation without removing the leg support device. In addition, the doctor can choose to install only the first support rod assembly 10d or the second support rod assembly 20d according to the convenience of operation, without having to install both, reducing operation steps and occupied operation space near the knee joint. The position of the support rod assembly on the slide rail can also be adjusted through the slider at the bottom, which can adapt to more clinical conditions.

The first support rod assembly 10d and the second support rod assembly 20d can be slidably connected with the base 90d, the first support rod assembly 10d and the second support rod assembly 20d can slide relative to the base 90d, and the position of the legs can be fine-tuned; A locking mechanism may also be provided between the first support rod assembly 10d, the second support rod assembly 20d and the base 90d for locking the relative positions of the first support rod assembly 10d, the second support rod assembly 20d and the base 90d.

Figure 2:
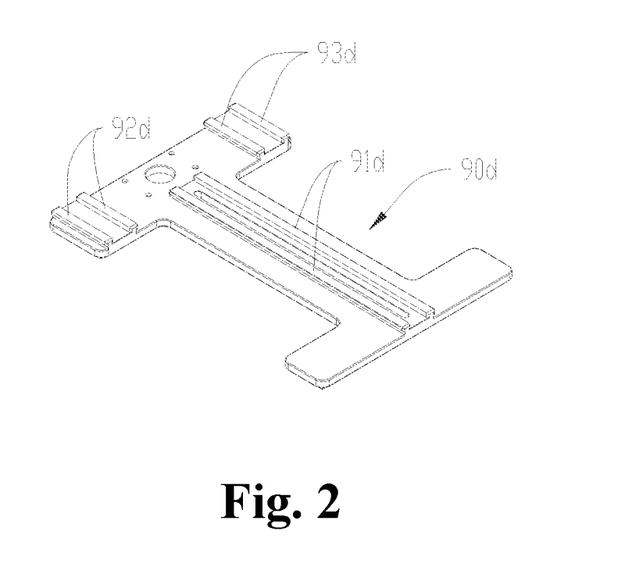
FIG. 2 is a structural schematic diagram of the base in FIG. 1.

Referring to FIG. 2, specifically, the base 90d is an I-shaped bottom plate with a first slide rail 91d in the middle, and a second slide rail 92d and a third slide rail 93d are respectively provided on both sides of one end of the first slide rail 91d.

The first support rod assembly 10d and the second support rod assembly 20d are symmetrically arranged on both sides of the first sliding rail 91d, and the two needle clamping devices are also symmetrically arranged.

Figure 3:
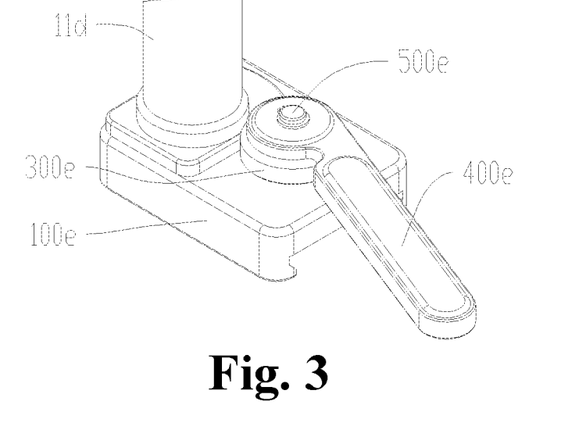
FIG. 3 is a schematic diagram of the structure of the vertical cylinder in FIG. 1 connecting with the base.
Figure 4:
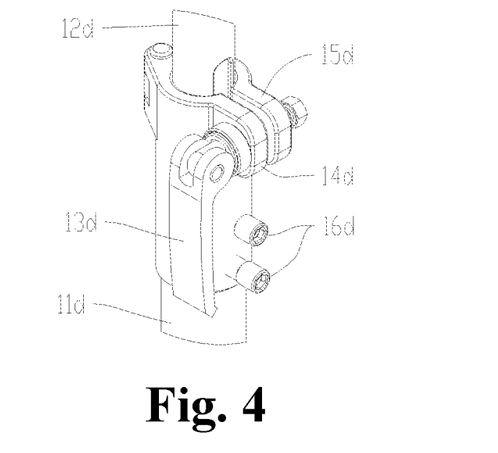
FIG. 4 is a structural schematic diagram between the vertical cylinder and the upright column in FIG. 1.

Referring to FIG. 1, FIG. 3 and FIG. 4, the structural composition of the first support rod assembly 10 d are taken as an example to describe below.

The lower end of the vertical cylinder 11d is connected to the second sliding rail 92d of the base 90d through the second sliding block 100e, and is controlled by the locking block 300e, the locking block driver 400e and the pin 500e to be locked with the second sliding rail 92d. The structures and their connection relationships of the second sliding block 100e, the locking block 300e, the locking block driving member 400e and the pin 500e are the same as the structure and its deformation of the sliding block 100m, the locking block 300m, the locking block driving member 400m and the pin 500m.

The upper end of the vertical cylinder 11d is provided with a clamping device, and the clamping device can lock the upright column 12d inserted into the vertical cylinder 11d. The clamping device includes a cam handle 13d, a first clamping arm 14d, a second clamping arm 15d and a locking screw 16d. One end of the first clamping arm 14d is hingedly connected with one end of the second clamping arm 15d, an arc-shaped clamping portion is provided in the middle of the two, and a gap is formed between the other ends. The cam handle 13d is provided at the position where the two clamping arms are provided with a gap, and the distance between the clamping arms is changed by the cam portion to realize the clamping effect. The cam handle 13d, the nut, the rotating shaft and the like constitute a cam handle assembly for realizing the clamping of the clamping arm. The locking screw 16d can also lock the vertical column 12d in the vertical cylinder 11d from the radial direction. Of course, the above locking mechanism is not unique, for example, the locking screw 16d may not be provided, or only the locking screw 16d may be provided, or the clamping structure in the needle clamping device may be used.

The upright column 12d is inserted into the upright cylinder 11d, and the cam handle 13d can be released when needed to adjust the insertion depth, thereby changing the height of the needle clamping device at the top of the upright post 12d relative to the base 90d.

In some optional embodiments, the first support rod assembly 10d can also be replaced with a support rod/arm with a fixed length, that is, the vertical cylinder 11d is fixedly connected with the vertical column 12d, and the lengths of the vertical cylinder 11d and the vertical column 12d are not adjustable in the axial direction.

In some optional embodiments, the first support rod assembly 10d and the second support rod assembly 20d may also be connected to the base 90d in other ways. For example, it is directly fixed on the base 90d with screws, bolts or other fastening structures.

In some optional embodiments, only the first support rod assembly 10d or the second support rod assembly 20d may also be provided. In use, the first support rod assembly 10d can be installed on the first slide rail 91d or the second slide rail 92d on the base 90d according to actual needs. Specifically, the first support rod assembly 10d can be installed on the third slide rail 93d in the attitude shown in FIG. 1; or the first support rod assembly 10d can be rotated 180 degrees around its long axis relative to the attitude shown in FIG. 1, and then installed on the third sliding rail 93d, so that the needle clamping device is still located outside, which is convenient for operation.

The first needle clamping device and the second needle clamping device are disposed on the top of the first support rod assembly 10d and the second support rod assembly 20 respectively. The first needle clamping device is capable of clamping the first threaded needle 1. Before clamping the first threaded needle 1, the first needle clamping device has two rotational degrees of freedom relative to the first support rod assembly 10d, and the operator can flexibly adjust the direction of the first threaded needle 1 as required. After the first threaded needle 1 is implanted in the affected limb, the first threaded needle 1 can be clamped and locked between the first needle clamping device and the first support rod assembly 10d by only one tightening, which is easy and convenient to operate. The second needle clamping device also has the above-mentioned connection relationship with the second threaded needle.

In some optional embodiments, the second needle clamping device can also be replaced with other form of needle clamping devices; in some other optional embodiments, the second needle clamping device can also be replaced with a fastening mechanism such as a bandage. As long as the first needle clamping device is provided, the complicated degree of the operation in the process of locking and releasing the threaded needle can be reduced to a certain extent.

The inventors of the present application have found that the fixing manner of the threaded needle used in the related art requires that the access of the threaded needle needs to be adjusted in multiple directions before implanting the threaded needle, and after implanting the threaded needle needs to be fixed on the fixing device and the parts of the fixing device itself needs to be locked. The above operations are not conducive to reducing the complicated degree of the surgery.

Figure 5:
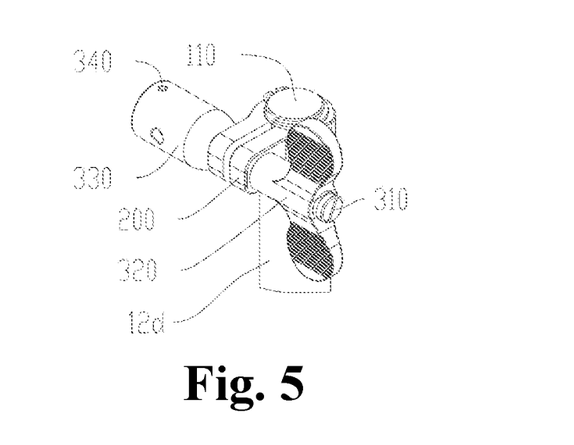
FIG. 5 is a structural schematic diagram of the needle clamping device in FIG. 1.
Figure 6:
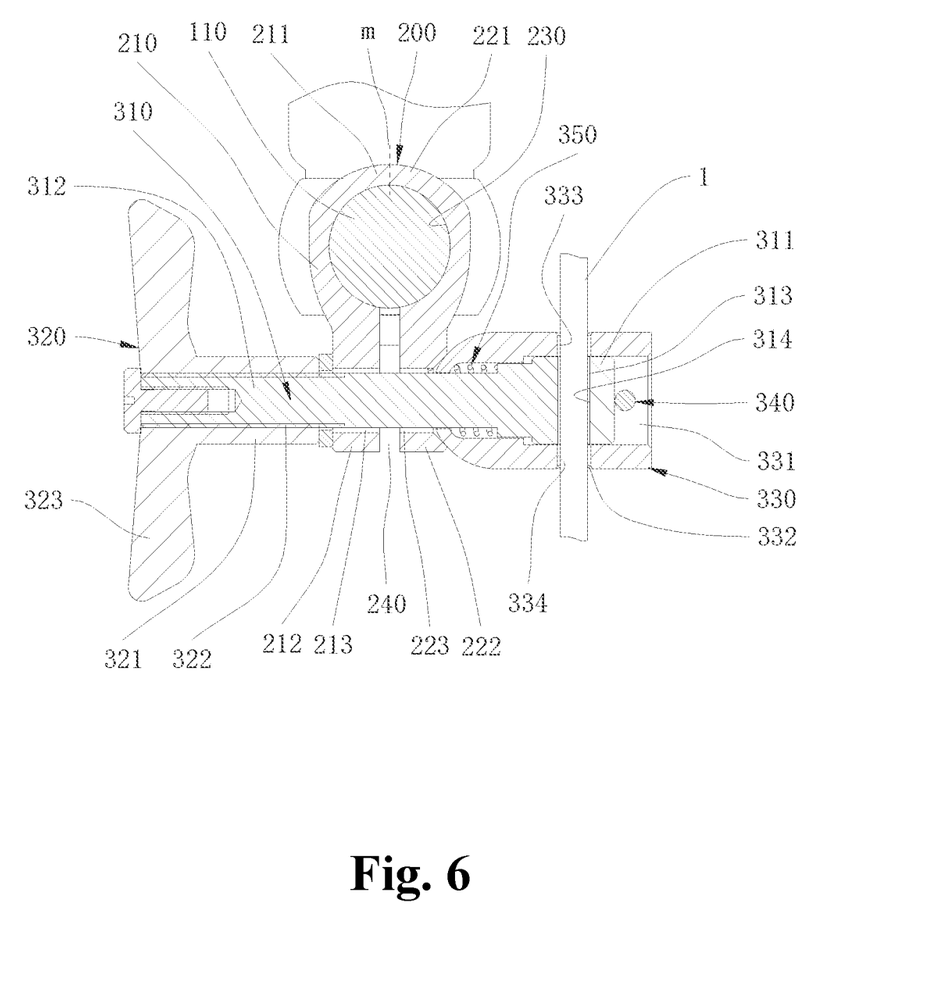
FIG. 6 is a cross-sectional view schematically showing the structure of the needle clamping device of FIG. 5.

In view of the above findings, embodiments of the present application also provide a needle clamping device for clamping an orthopedic needle, which can at least reduce the complicated degree of operations in the process of locking and releasing the threaded needle. In order to facilitate the understanding of the needle clamping device of embodiments of the present application, the needle clamping device, the first needle-clamping device, and the second needle-clamping device of embodiments of the present application are described further in combination with FIG. 5 and FIG. 6, taking the first needle-clamping device as an example. FIG. 5 is a structural schematic diagram of the first needle clamping device in FIG. 1; FIG. 6 is a cross-sectional view of the first needle clamping device, wherein the cutting plane passes through the centerline of the first threaded needle 1 and is perpendicular to the first support rod assembly.

The first needle clamping device includes a first component 100, a second component 200 and a clamping mechanism 300. The first component 100 is provided on the first support rod assembly 10d. In the unlocked state, the second component 200 can be rotated relative to the first component 100, the clamping mechanism 300 as a whole can be rotated relative to the second component 200, and the axes of the two rotational movements are in a spatially vertical relationship. The above connection relationship is convenient for adjusting the implanted device to a proper implantation orientation before the implantation operation.

The first component 100 includes a shaft portion 110. The shaft portion 110 is disposed at the top end of the first support rod assembly 10d. The peripheral surface of the tail end of the shaft portion 110 is provided with a ring groove for installing a snap ring to limit axially.

The second component 200 is hinged with the shaft portion 110, the second component 200 includes a first portion and a second portion whose relative positions are variable, and the first portion and the second portion are arranged to clamp the shaft portion 110 when the relative position changes. In some embodiments, the first and second portions of the second component are first and second clamping arms 210 and 220 disposed side by side. The first end portion 211 of the first clamping arm 210 is connected to the first end portion 221 of the second clamping arm 220. There is a predetermined distance, that is, a gap 240, between the second end portion 212 of the first clamping arm 210 and the second end portion 222 of the second clamping arm 220. A shaft hole 230 is further provided between the first clamping arm 210 and the second clamping arm 220.

In the illustrated embodiments, the second component 200 is an open ring structure, which can be made by milling holes and slitting on a roughly cuboid blank, and the slit is arranged on the solid structure around the hole along the radial direction of the hole and is in communication with the hole. The solid structure around the hole is the main ring body, and the solid structures on both sides of the slit can be regarded as extension portions of the two tail ends of the main ring body respectively pointing to the outside of the ring body (the second end portion 212 and the second end portion 222). The first clamping arm 210 is a half structure of the open ring structure (the left half portion of the dotted line m in FIG. 6), including half of the main ring body and its extension portion (the second end portion 212). The second clamping arm 220 is the other half structure of the open ring structure (the right half portion of the dotted line m in FIG. 6), including the other half of the main ring body and its extension portion (the second end portion 222). The shaft hole 230 is a ring hole of the open ring structure. The open ring structure is an integral structure, and the first end portion 211 of the first clamping arm 210 is fixedly connected with the first end portion 221 of the second clamping arm 220.

The second end portion 212 of the first clamping arm 210 is provided with a through hole 213, and the through hole 213 is perpendicular to the shaft hole 230. The second end portion 222 of the second clamping arm 220 is provided with a through hole 223, and the through hole 223 is coaxially aligned with the through hole 213.

The shaft hole 230 of the second component 200 has the same diameter as the shaft portion 110 of the first component 100, and the two form a rotational connection through the shaft hole engagement. When the second end portion 212 and the second end portion 222 are brought close to each other, the diameter of the shaft hole 230 tends to decrease, so the first clamping arm 210 and the second clamping arm 220 can clamp the shaft portion 110 to achieve locking function.

The clamping mechanism 300 is used for clamping the needle, the clamping mechanism 300 is connected to the second component 200, the clamping mechanism 300 is configured that at least part of the structure clamps the first portion and the second portion, and in the process of clamping the orthopaedic needle the first portion and the second portion are driven to change the relative position so that the second component 200 clamps the shaft portion 110. In some embodiments, the clamping mechanism 300 may include an inner shaft 310, a handle member 320, a locking sleeve 330, a limit pin 340 and a spring 350.

The inner shaft 310 penetrates through the second end portion 212 and the second end portion 222 of the second component. The first end 311 and the second end 312 of the inner shaft 310 are distributed on both sides of the second component 200, and the first end 311 is provided with a first limiting surface 314. The outer circumferential surface of the second end 312 is provided with threads.

Specifically, the inner shaft 310 is inserted into the second end portion 212 and the second end portion 222 through the through hole 213 and the through hole 223, the first end 311 protrudes from one side of the second end portion 222, and the second end 312 protrudes from one side of the second end portion 212. The tail end section of the first end 311 is a square shaft, the outer peripheral surface of this section is four planes, and a transition step is further provided between this section and the second end 312. The square shaft is further provided with a first radial hole 313. The first limiting surface 314 is the hole wall portion of the first radial hole 313 facing the second end 312, that is, the right half portion of the hole wall of the first radial hole 313 in the figure. When the first threaded needle 1 is locked, the hole wall portion contacts and presses the first threaded needle 1, so it is defined as the first limiting surface. Part of the wall surface of the round hole is an implementation manner of the first limiting surface, and in some optional embodiments, the first radial hole 313 may also be a recessed structure arranged radially such as a waist-shaped hole, a square hole, or a groove. T the first limiting surface is the hole wall portion facing the second end 312 in the above structure, and the hole wall portion may be a plane or a curved surface.

The handle member 320 is movably disposed on the second end 312 of the inner shaft 310, and the handle member 320 can move axially on the inner shaft 310 as a whole when the handle member 320 moves relative to the inner shaft 310. Specifically, the handle member 320 includes a cylinder portion 321, a handle portion 323 and a threaded hole 322. The handle portion 323 protrudes from the outer surface of the cylinder portion 321 in the radial direction. The threaded hole 322 penetrates the cylinder portion 321. The handle member 320 forms a nut-screw mechanism through the threaded hole 322 and the external thread of the inner shaft 310. When the handle member 320 rotates on the inner shaft 310, the handle member 320 can move axially on the inner shaft 310 at the same time.

The center of the locking sleeve 330 is provided with a through hole 331, and the through hole 331 is a stepped hole. The locking sleeve 330 has a second limiting surface 333 and a second limiting surface 334, which are arranged diagonally opposite to the first limiting surface 314 of the inner shaft 310. Specifically, the through hole 331 is a square hole at the maximum diameter thereof (the right half portion of FIG. 6), whose size matches the square shaft of the first end 311 of the inner shaft 310 and forms a circumferential limiting engagement with the square shaft. The locking sleeve 330 is provided with a second radial hole 332 penetrating in the radial direction. The hole is divided into two sections by the through hole 331. The second limiting surface 333 and the second limiting surface 334 are the hole wall portions of the two sections having the same direction as the end surface of the first end 311. When the first threaded needle 1 is locked, the hole wall portions will contact and press against the first threaded needle 1, so it is defined as the second limiting surface. Part of the wall surface of the round hole is only an implementation manner of the second limiting surface, and in some optional embodiments, the second radial hole 332 may also be a recessed structure arranged radially such as a waist-shaped hole, a square hole, or a groove, etc. The second limiting surface is the hole wall portion of the recessed structure that has the same direction as the end surface of the first end 311 (the hole wall portion facing away from the second component 200), and the hole wall portion may be a plane or a curved surface. The locking sleeve 330 is sleeved outside the first end 311 of the inner shaft 310. The locking sleeve 330 is axially movable relative to the inner shaft 310.

The locking sleeve 330 is also provided with a radial hole for installing a limiting pin 340, and the radial hole is located outside the second radial hole 332 (the right side of the second radial hole 332 in FIG. 6). The limiting pin 340 is inserted into the radial hole of the locking sleeve 330 and is located outside the end surface of the first end 311 to form a structure of limiting the axial direction of the inner shaft 310.

The spring 350 is sleeved on the inner shaft 310 and is located in the through hole 331 of the locking sleeve 330. One end of the spring 350 abuts against a step of the through hole 331, and the other end abuts against the shoulder of the transition step of the inner shaft 310. The spring 350 causes the first end 311 has tendency to protrude outward (rightward in FIG. 6) from the through hole 331 (the tendency to move the locking sleeve 330 toward the side of the second end 312 of the inner shaft 310).

The handle member 320 and the locking sleeve 330 are located on two sides of the second component 200 respectively. Both the handle member 320 and the locking sleeve 330 can move along the axial direction of the inner shaft 310. When the handle member 320 and the locking sleeve 330 are close to each other, the second component 200 can clamp the shaft portion 110 under the clamping of the handle member 320 and the locking sleeve 330, eliminating the two rotational degrees of freedom of the first needle clamping device.

Embodiments of the present application only need to drive the handle to realize the locking of the threaded needle and the locking of the two rotational degrees of freedom of the needle clamping device, which is convenient to operate and saves time and effort.

Instructions for use:

The handle member 320 is rotated so that the distance from the locking sleeve 330 becomes larger. In this process, under the action of the spring 350, the first end 311 of the inner shaft 310 approaches the limit pin 340 and finally abuts against the limit pin 340. At this time, the second radial hole 332 is aligned with the first radial hole 313 and the first threaded needle 1 is inserted.

The orientation of the first threaded needle 1 is adjusted until an appropriate implantation path is reached, and a tool is used to drive the first threaded needle 1 into the patient's bone.

The handle member 320 is rotated so that it is close to the locking sleeve 330. In this process, the inner shaft 310 will pull the first threaded needle 1 and the locking sleeve 330 to approach the handle member 320 together. The locking sleeve 330 acts on the second end portion 222 of the second component 200, and the handle member 320 acts on the second end portion 212, so that the first clamping arm 210 and the second clamping arm 220 clamp the shaft portion 110. In addition, the first limiting surface 314 of the inner shaft 310 and the second limiting surface 334 and the second limiting surface 333 of the locking sleeve 330 jointly clamp the first threaded needle 1, so that the first threaded needle 1 cannot move or turn. In some other embodiments, the handle member 302 can also be a nut, the nut is connected with the second end 312 of the inner shaft 310 by a thread, and the nut can drive the first clamping arm 210 and the second clamping arm 220 to clamp the shaft portion 110 of the first component when the nut moves along the inner shaft 310 and approaches the locking sleeve 330.

In the above operation process, the clamping mechanism 300 has two rotational degrees of freedom relative to the first component 100, so the adjustment range of the threaded needle is relatively large. The first threaded needle 1 can be clamped between the inner shaft 310 and the locking sleeve 330 only by turning the handle member 320, so that the inner shaft 310 and the handle member 320 are also locked with the second component 200 and the second component 200 is locked with the first component 100, which is convenient to operate and saves time and effort. In addition, in the process of driving the first threaded needle 1 into the patient's bone, the first radial hole 313 and the second radial hole 332 in the clamping mechanism 300 can further guide and support the first threaded needle 1, and the operator can grip the clamping mechanism 300 to prevent the first threaded needle 1 from being offset. The cooperation of the limiting pin 340 and the spring 350 can further automatically align the second radial hole 332 with the first radial hole 313, so as to facilitate the rapid insertion of the first threaded needle 1. The contact line between the first threaded needle 1 and the first radial hole 313 is parallel to the contact line between the first threaded needle 1 and the second radial hole 332 and the contact line is long, so that the first threaded needle 1 is evenly stressed and locked reliable. In some optional embodiments, the spring 350 may not be provided. During the operation, the operator can move the locking sleeve 330 to make the limiting pin 340 abut against the end surface of the first end 311, and manually align the second radial hole 332 with the first radial hole 313.

In some optional embodiments, the limiting pin 340 and the spring 350 may not be provided. The second radial hole 332 is manually aligned with the first radial hole 313 during operation.

In some optional embodiments, no circumferential limit may be provided between the inner shaft 310 and the locking sleeve 330, and the second radial hole 332 and the first radial hole 313 may be manually rotated and aligned during operation.

In some optional embodiments, the circumferential limit between the inner shaft 310 and the locking sleeve 330 may be the cooperation of a guide groove along the axial direction of the inner shaft 310 and a key provided on the locking sleeve 330; or, one or two flat surfaces are provided on the peripheral surface of the first end 311, and corresponding matching structures are provided on the locking sleeve 330. The matching structure of the locking sleeve 330 may be formed by machining, or additional parts may be provided on the locking sleeve 330, and part of the surface of the part forms a matching structure (such as the end surface or the outer peripheral surface of a pin or a nail, the flat surface of a key).

Figure 7:
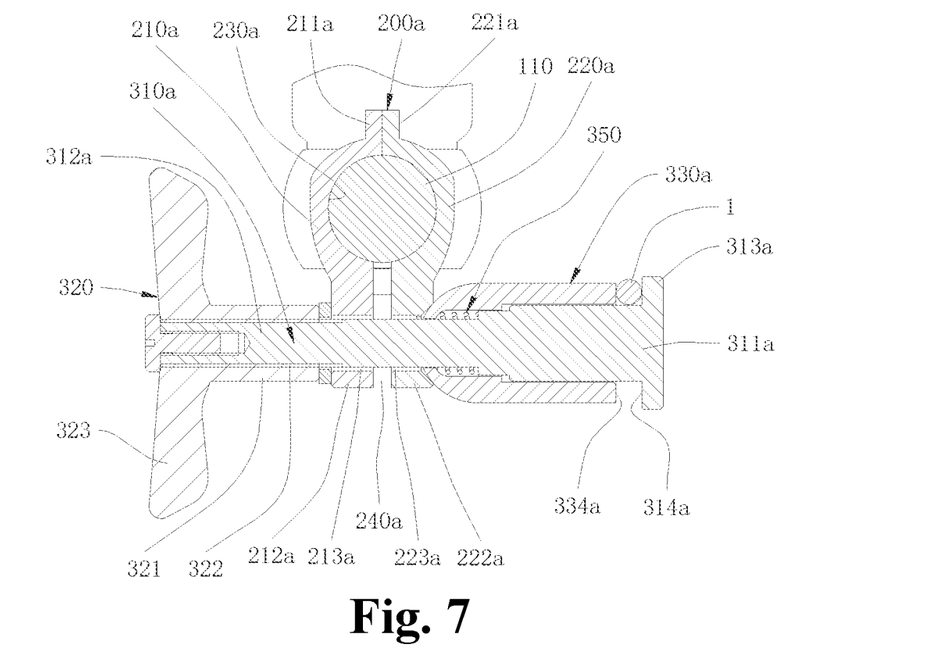
FIG. 7 is a cross-sectional view schematically showing the structure of the needle clamping device in another embodiment.

Referring to FIG. 7, FIG. 7 is a schematic structural diagram of a needle clamping device in another embodiment. The structure of the needle clamping device in the present embodiment is basically the same as the structure and principle of the first needle clamping device shown in FIG. 6, the difference include the second component 200a is a split structure, and the second component 200 is an integral structure; the inner shaft 310a and the locking sleeve 330a are not provided with radial holes, but the first threaded needle 1 is clamped by the gap between them; and there is no limit pin between the inner shaft 310a and the locking sleeve 330a to perform axial limit. The structural differences of the second component 200a, the inner shaft 310a and the locking sleeve 330a will be specifically described below.

The second component 200a is formed by connecting two separate clamping arms, and the two clamping arms are the first clamping arm 210a and the second clamping arm 220a in the figure. The first clamping arm 210a includes a half ring body in the middle and a first end portion 211a and a second end portion 212a at both ends of the half ring body, and the second end portion 212a is longer than the first end portion 211a. The second clamping arm 220a includes a half ring body in the middle and a first end portion 221a and a second end portion 222a at both ends of the half ring body, and the second end portion 222a is longer than the first end portion 221a. The first clamping arm 210a and the second clamping arm 220a are fastened together, the two half ring bodies form an open ring body, and the center of the ring body is the shaft hole 230a. The first end portion 211a is fixedly connected to the first end portion 221a. The second end portion 212a is provided with a through hole 213a. The second end portion 222a is provided with a through hole 223a. A gap 240a is formed between the second end portion 212a and the second end portion 222a.

In some optional embodiments, the first end portion 211a may also be hingedly connected to the first end portion 221a.

The inner shaft 310a is different from the inner shaft 310 in that the first radial hole 313 is not provided, but a flange 313a is formed at the tail end of the first end 311a. The side surface of the flange 313a facing the second end 312a is the first limiting surface 314a. In the assembly body, the flange 313a protrudes out of the end surface of the locking sleeve 330a, the first limiting surface 314a faces the second limiting surface 334a, and a ring groove is formed therebetween.

The difference between the locking sleeve 330a and the locking sleeve 330 is that the second radial hole 332 and the radial hole for installing the limiting pin 340 are not provided. The end surface of the locking sleeve 330a that is not adjacent to the second component 200a is the second limiting surface 334a.

When the handle member 320 is rotated, there is an axial relative displacement between the inner shaft 310a and the locking sleeve 330a, so that the first threaded needle 1 can be clamped or released. A recessed groove can also be provided on the side of the flange 313a to prevent the first threaded needle 1 from coming out in the radial direction.

In some optional embodiments, the inner shaft 310a and the second component 200a cannot rotate relative to each other. The position of the first threaded needle 1 in the annular groove formed by the first limiting surface 314a and the second limiting surface 334a is adjustable, so there is no need for rotational freedom between the inner shaft 310a and the second component 200a.

In some optional embodiments, the inner shaft 310a and the second component 200a cannot rotate relative to each other, there is no circumferential limit between the locking sleeve 330a and the inner shaft 310a, and the locking sleeve 330a and the inner shaft 310a can rotate relative to each other. In some other optional embodiments, the inner shaft 310a and the second component 200a cannot rotate relative to each other, there is no circumferential limit between the locking sleeve 330a and the inner shaft 310a, and the locking sleeve 330a and the inner shaft 310a can rotate relative to each other, and a recessed groove is provided on the end surface of the locking sleeve 330a. When the first threaded needle 1 is located in the recessed groove, the locking sleeve 330a can follow the rotation of the first threaded needle 1 around the inner shaft 310a. This can not only ensure that the position of the first threaded needle 1 can be adjusted, but also prevent the first threaded needle 1 from coming out.

Figure 8:
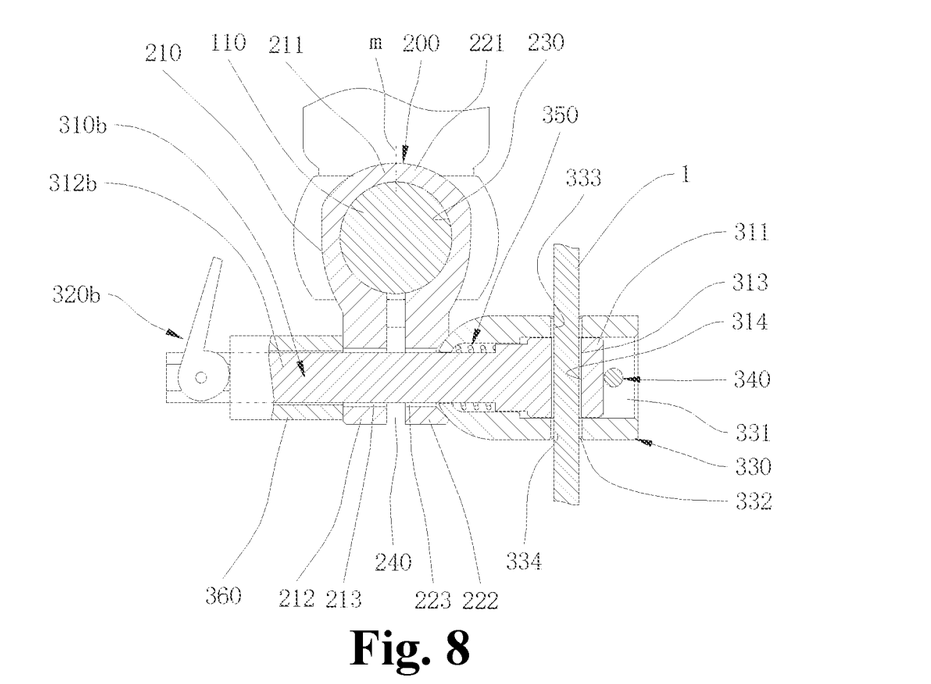
FIG. 8 is a cross-sectional view schematically showing the structure of the needle clamping device in another embodiment.

Referring to FIG. 8, FIG. 8 is a schematic structural diagram of a needle clamping device in another embodiment. Compared with the first needle clamping device shown in FIG. 6, the needle clamping device in the present embodiment uses the cam handle 320b instead of the handle member 320 to realize the locking function. Specifically, a cam handle 320b and a sleeve 360 are disposed on the second end 312b of the inner shaft 310b, and the sleeve 360 is located between the second component 200 and the cam handle 320b. When the cam handle 320b rotates, the sleeve 360 can be driven to squeeze the second component 200 so as to achieve locking. The cam handle 320b includes a cam portion and a handle portion, the cam portion is rotatably disposed on the second end 312b, and the rotation center line is perpendicular to the inner shaft 310b. When the cam handle 320b is toggled, the contour surface of the cam portion rotates along with it, and its rotational motion can be decomposed into the movement along the axial direction of the inner shaft 310b, the movement and rotation along the radial direction of the inner shaft 310b, which is equivalent to the movement of part of the structure of the cam handle 320b along the axial direction of the inner shaft 310b.

In some optional embodiments, the sleeve 360 may not be provided, and the cam handle 320b may directly act on the second component 200. In some other optional embodiments, a cylindrical cam can also be used to replace the cam handle 320b. The cylindrical cam and the inner shaft 310b are coaxially arranged and can rotate relative to each other. The cam surface of the cylindrical cam is located on the end surface of the cylinder and faces the sleeve 360 in the assembly body, and the sleeve 360 is provided with a protrusion facing the cam surface. When the cylindrical cam is rotated, the interaction between the cam surface and the sleeve 360 causes an axial displacement therebetween, thereby compressing the second component 200.

The leg support device of embodiments of the present application may further include a foot support 30, and the foot support 30 is installed on the base 90d. The foot support 30 can accommodate the foot of the patient, and the foot support 30 is slidably connected with the base 90d, and the position of the foot support 30 relative to the base 90d can be adjusted.

Specifically, the foot support 30 is connected to the first sliding rail 91d by the foot support positioning device. The structures of the foot support 30, the foot support positioning device and the connection between them are the same as those shown in FIGS. 9 to 14, and the specific structures can refer to the drawings and their descriptions, which will not be repeated here.

Figure 9:
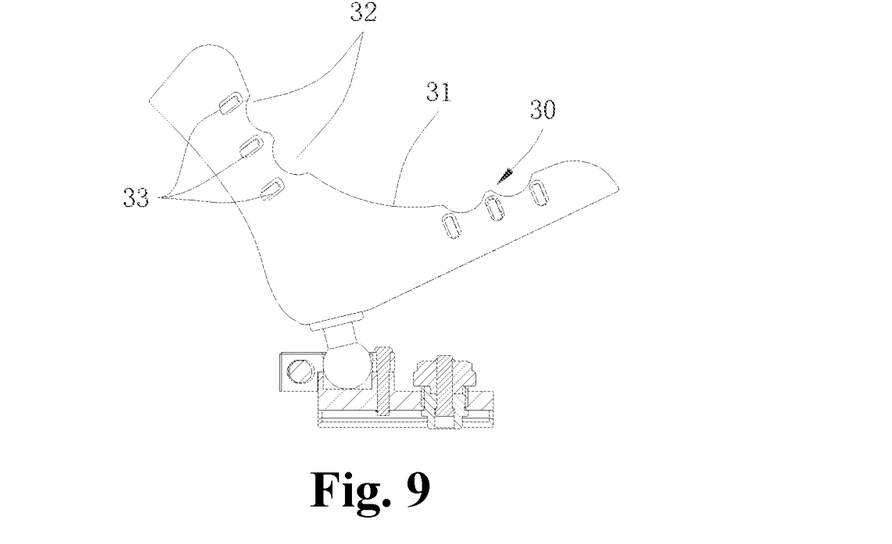
FIG. 9 shows a structural schematic diagram of the foot support positioning device in FIG. 1 and the cross-sectional view of the foot support.
Figure 10:
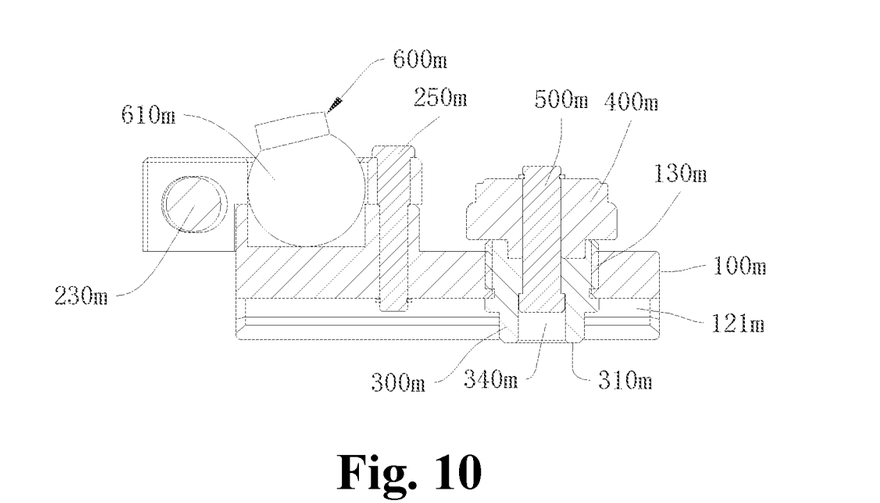
FIG. 10 is an enlarged view of the foot support positioning device in FIG. 9.
Figure 11:
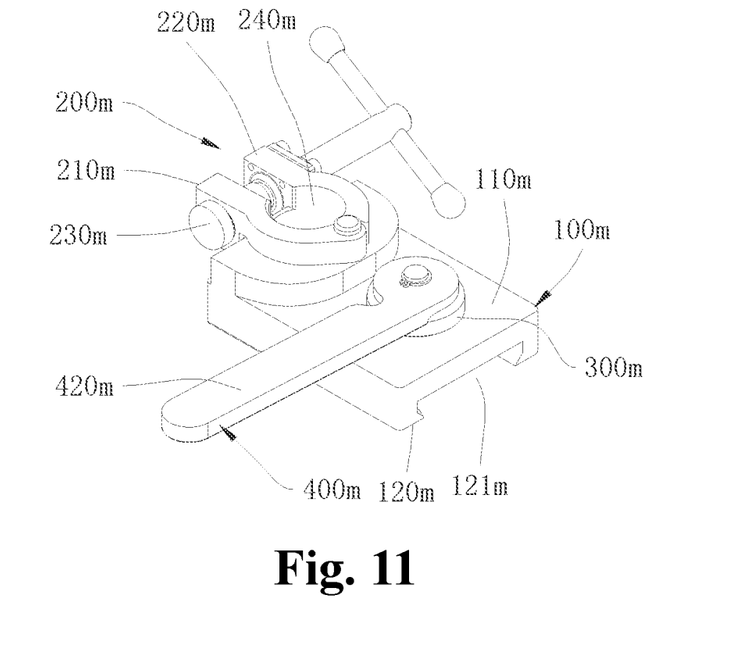
FIG. 11 is a perspective view of the foot support positioning device in FIG. 1.
Figure 12:
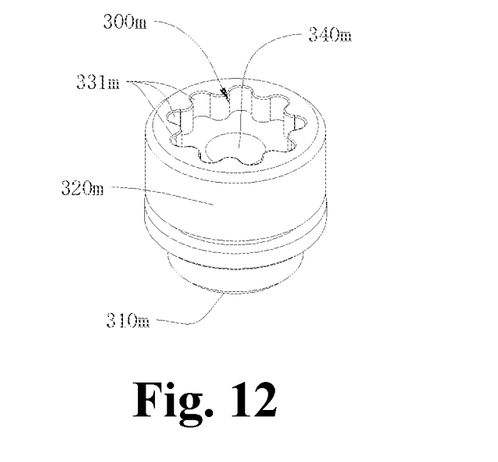
FIG. 12 is a structural schematic diagram of the locking block in FIG. 1.
Figure 13:
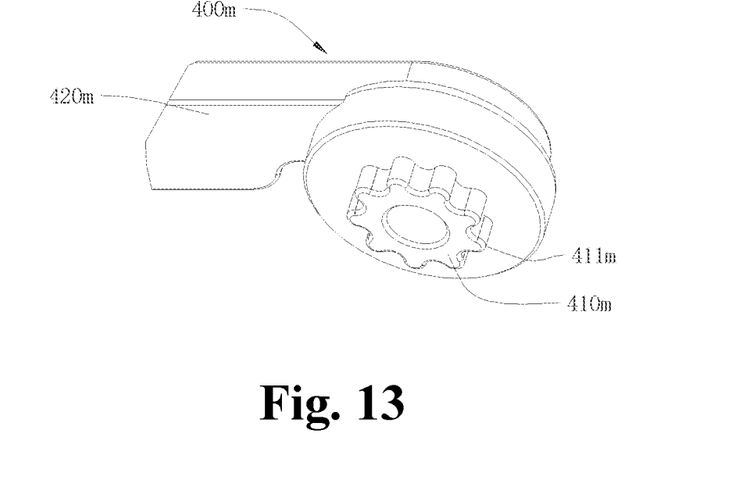
FIG. 13 is a structural schematic diagram of the locking block driver in FIG. 1.

Referring to FIGS. 9 to 13, FIG. 9 is a cross-sectional view of the foot support positioning device and the foot support 30 in FIG. 1; FIG. 10 is an enlarged view of the foot support positioning device in FIG. 9; FIG. 11 is a perspective view of the foot support positioning device in FIG. 1; FIG. 12 is a schematic structural diagram of the locking block 300m in FIG. 1; FIG. 13 is a schematic structural diagram of the locking block driver 400m in FIG. 1.

The foot support positioning device includes a sliding block 100m, a foot support connecting mechanism 200m, a locking block 300m, a locking block driver 400m, and a pin 500m. The sliding block 100m is the base for bearing and installation, and the foot support connection mechanism 200m, the locking block 300m, the locking block driver 400m and the pin 500m are all disposed on the sliding block 100m.

The sliding block 100m is a rectangular plate structure. The bottom 120m of the sliding block 100m is provided with a chute 121m, and the chute 121m is a dovetail slot. The upper surface of the sliding block 100m is the load surface 110m, the load surface 110m is provided with a threaded hole 130m and a boss, and the boss is provided with a pin hole and a recessed portion. Both the pin hole and the threaded hole 130m are perpendicular to the plate body, and the threaded hole 130m is a through hole. The sliding block 100m is movably disposed on the sliding rail 12 of the base 90d through the chute 121m.

The foot support connecting mechanism 200m includes a first tong arm 210m, a second tong arm 220m, a locking screw 230m and a pin 250m, and an accommodating cavity 240m is provided between the first tong arm 210m and the second tong arm 220m. The second tong arm 220m is fixedly connected to the sliding block 100m, and in the present embodiment, they are integral structure. The first tong arm 210m is hingedly connected with the pin 250m, and is connected in the pin hole of the boss through the pin 500m. The accommodating cavity 240m corresponds to the recessed portion on the boss of the sliding block 100m. The other ends of the first tong arm 210m and the second tong arm 220m are both provided with through holes, the through hole of the first tong arm 210m is a waist-shaped hole, and the through hole of the second tong arm 220m is a threaded hole. The threaded hole of the second tong arm 220m is a threaded hole of a nut embedded in the second tong arm 220m, and the material of the nut can be a wear-reducing material. One end of the locking screw 230m is provided with a nut, the other end is provided with a radial through hole, and a thread is provided in the middle. The locking screw 230m is inserted into the through holes of the first tong arm 210m and the tong clamp arm 220m, and the threaded section of the locking screw 230m and the threaded hole of the second tong arm 220m constitute a nut screw pair. The radial hole of the locking screw 230m is provided with a lever, and the lever is used to rotate the locking screw 230*m*. In some optional embodiments, the second tong arm 220*m* is a separate part, one end of each of the first tong arm 210*m* and the second tong arm 220*m* is hinged into one body through a pin 250*m*, and connected to the sliding block 100*m* through a pin 250*m*.

The connection structure for clamping the foot support 30 is disposed in the accommodating cavity 240*m* of the foot support connecting mechanism 200*m*. In the present embodiment, the connection structure of the foot support 30 is a foot support connecting rod 600*m*, and the tail end of the foot support connecting rod 600*m* is provided with a ball head 610*m*.

The locking block 300*m* includes a locking portion 310*m*, an external thread portion 320*m* and a drive interface portion 330*m*. The locking block 300*m* is a cylinder, the locking portion 310*m* and the external thread portion 320*m* are provided at both ends of the cylinder, and the external thread portion 320*m* is provided on the outer peripheral surface of the cylinder. A through hole is further provided in the center of the cylinder. The locking portion 310*m* is the end surface of the cylinder, and the end surface is used to abut the upper surface of the base 90*d*. The drive interface portion 330*m* is a quincunx groove on the other end surface of the cylinder. The quincunx groove has an annular array of torque transmission portions 331*m*, and the torque transmission portions 331*m* are recessed grooves along the radial direction of the cylinder, which can generate a torque of 300*m* on the locking block when the side wall of the recessed groove is forced. In the present embodiment, the number of recessed grooves of the quincunx groove is nine and the array angle interval of the recessed grooves is 40 degrees. The nine recessed grooves can be regarded as a set of torque transmission portions. The locking block 300*m* is disposed in the threaded hole 130*m* of the sliding block 100*m* through the external thread portion 320*m*.

The locking block driver 400*m* includes a torque output portion 410*m* and a handle portion 420*m*. Specifically, one tail end of the handle portion 420*m* is provided with a disc, and an end surface of the disc is provided with the torque output portion 410*m*. The torque output portion 410*m* is a gear-shaped structure having an annular array of teeth 411*m*. A through hole is provided in the center of the gear-shaped structure. The outer contour of the torque output portion 410*m* is the same as that of the drive interface portion 330*m*, the torque output portion 410*m* is embedded in the drive interface portion 330*m*, and the teeth 411*m* of the torque output portion 410*m* are embedded in the recessed grooves of the quincunx groove of the drive interface portion 330*m*. The through hole 340*m* is coaxial with the through hole of the locking block driver 400*m*.

The pin 500*m* is inserted into the through hole of the locking block 300*m* and the locking block driver 400*m*, and limits the radial displacement between the locking block 300*m* and the locking block driver 400*m* together with the shaft snap ring.

When the locking block 300*m* is driven to rotate by the locking block driver 400*m*, the locking block 300*m* can move axially relative to the sliding block 100*m* and abut against the base 90*d*, so that the sliding block 100*m* is fixed on the base 90*d*.

Upon assembly, the azimuth relationship between the locking block driver 400*m* and the locking block 300*m* can be set according to actual needs. For example, during the locking operation, the handle needs to be rotated, and the required force is the largest just before reaching the locking position. If the operating space of the handle is relatively small near the locking position, it will cause inconvenience in operation. It is therefore necessary to set the handle to have sufficient space between the handle and the surrounding structure in the locked state. Specifically, in the present solution, the locking block driver 400*m* is located below the foot support 30, so the position of the locking block driver 400*m* shown in FIG. 11 is in a locked state for convenient operation. Upon assembly, the foot support 30 is not installed first, the locking block 300*m* is screwed into the threaded hole 130*m* of the sliding block 100*m*, the pin 500*m* is inserted into the through hole 340*m* of the locking block 300*m*, and then the sliding block 100*m* is installed on the slide rail 12. The locking block driver 400*m* is used to rotate the locking block 300*m* to lock the sliding block 100*m*. At this time, the position of the locking block driver 400*m* relative to the sliding block 100*m* can be arbitrary. The locking block driver 400*m* is took out, the lock block driver 400*m* at the position shown in FIG. 10 is installed, and then the locking block driver 400*m* is turned to release the locking block 300*m* from the base 90*d*, the sliding block 100*m* is removed, such that the pin 500*m* protrudes from the through hole of the locking block driver 400*m* and a snap ring is used to achieve axial limit.

In some optional embodiments, the torque output portion 410*m* may be provided with a smaller number of teeth 411*m*, such as three which are evenly distributed. In this case, the torque transmission portion 331*m* in the drive interface portion 330*m* is equivalent to three groups, and each group has three annular recessed grooves which are evenly distributed.

In some optional embodiments, the torque output portion 410*m* may be provided with a smaller number of teeth 411*m*, such as one, two, three or four, and the angular interval between the teeth 411*m* is 40 degrees (equivalent to removing some adjacent teeth 411*m* of torque output 410*m* in FIG. 12).

The foot support 30 is an "L"-shaped structure, which is similar to the shape of the foot and lower leg of a human body. The foot support 30 includes an "L"-shaped bottom plate and two side plates 31 on both sides of the bottom plate, and the space between the two side plates 31 is used for accommodating feet. The edge of the side plate 31 is provided with a notch 32, and the outer side of the side plate 31 is provided with a limiting protrusion 33. When the patient's foot is bound, the limiting protrusion 33 can prevent the bandage from slipping off. When the patient's foot is relatively thin, the bandage can pass through the notch 32, which can effectively fix the foot. The bottom of the foot support 30 is provided with a foot support connecting rod 600*m*, and the tail end of the foot support connecting rod 600*m* is provided with a ball head 610*m*. The foot support 30 is installed in the accommodating cavity 240*m* of the foot support connecting mechanism 200*m* through the ball head 610*m*, and the ball head 610*m* is clamped by the first tong arm 210*m* and the second tong arm 220*m*.

Figure 14:
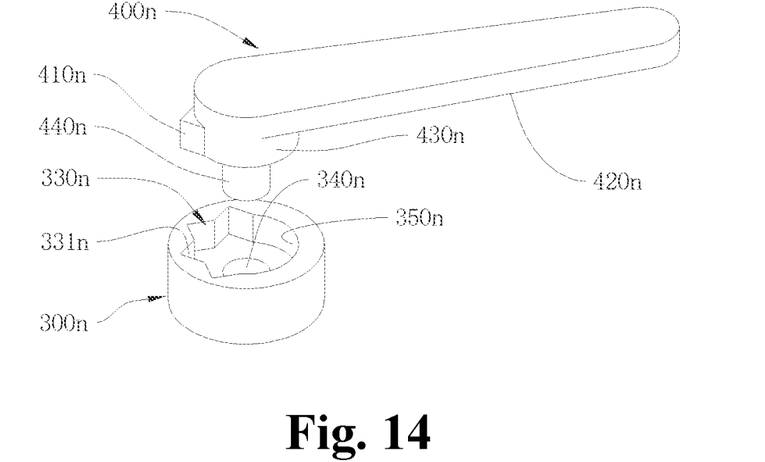
FIG. 14 is a structural schematic diagram of a locking block and a locking block driver in another embodiment.

Referring to FIG. 14, FIG. 14 is a schematic structural diagram of a locking block and a locking block driver in another embodiment.

In the present embodiment, the locking block driver 400*n* includes a torque output portion 410*n*, a handle portion 420*n*, a cylindrical base 430*n* and a positioning column 440*n*. The cylindrical base 430*n* is provided at the tail end of the handle portion 420*n*. The torque output portion 410*n* is provided on the outer circumferential surface of the cylindrical base 430*n*. The positioning column 440*n* is disposed on the lower end surface of the cylindrical base 430*n*. The drive interface portion 330*n* of the locking block 300n is a recessed groove on the end surface of the locking block 300n, and the side wall of the recessed groove includes an arc surface portion 350n and a plurality of torque transmission portions 331n. The torque transmission portion 331n is a recessed groove in the radial direction, and the shape is adapted to the torque output portion 410n. The locking block 300n is further provided with a through hole 340n coaxial with the arc surface portion 350n. The positioning post 440n can form a shaft hole matching with the through hole 340n. The cylindrical base 430n and the arc surface portion 350n are also cylindrical surface matching, so in some embodiments, the positioning column 440n may not be provided. Four torque transmission portions 331n are provided, so there are four relative positional relationships between the locking block driver 400n and the locking block 300n, which can be selected during assembly according to actual needs.

Although the present application has been described with reference to preferred embodiments, various modifications may be made and equivalents may be substituted for parts thereof without departing from the scope of the application, particularly, provided that no structural conflict exists, each technical feature mentioned in each embodiment can be combined in any manner. The present application is not limited to the specific embodiments disclosed herein, but includes all technical solutions falling within the scope of the claims.

What is claimed is:

1. A needle clamping device for clamping an orthopedic needle, wherein the needle clamping device comprises:
   a first component comprising a shaft portion;
   a second component hinged with the shaft portion, wherein the second component comprises a first portion and a second portion whose relative position is variable, and the first portion and the second portion are arranged to clamp the shaft portion when the relative position changes; and
   a clamping mechanism for clamping the needle, wherein the clamping mechanism is connected to the second component, the clamping mechanism is arranged so that at least part of the clamping mechanism further clamps the first portion and the second portion, and drives the first portion and the second portion to change their relative position so that the second component clamps the shaft portion in the process of clamping the orthopedic needle,
   wherein the first portion and the second portion of the second component are a first clamping arm and a second clamping arm arranged side by side, a first end portion of the first clamping arm is connected with a first end portion of the second clamping arm, a predetermined distance is formed between a second end portion of the first clamping arm and a second end portion of the second clamping arm, a shaft hole is formed between the first clamping arm and the second clamping arm; the second component is rotatably connected with the shaft portion of the first component through the shaft hole,
   wherein the clamping mechanism comprises:
      an inner shaft, wherein the inner shaft passes through the second end portion of the first clamping arm and the second end portion of the second clamping arm, a first end and a second end of the inner shaft are distributed on both sides of the second component, and the first end is provided with a first limiting surface;
      a handle member, wherein the handle member is movably disposed on the second end of the inner shaft, and when the handle member moves relative to the inner shaft, at least part of the handle member can move in an axial direction of the inner shaft; and
      a locking sleeve with a through hole, wherein the locking sleeve is sleeved on the outside of the first end of the inner shaft, the locking sleeve can move relative to the inner shaft, the locking sleeve comprises a second limiting surface, and the second limiting surface and the first limiting surface of the inner shaft are arranged face-to-face or diagonally opposite to each other,
   wherein the second component forms a limit for the handle member and the locking sleeve in the axial direction of the inner shaft, and
   wherein an elastic member is further provided between the first end of the inner shaft and the locking sleeve, and the elastic member acts on the inner shaft and configures the inner shaft to have a tendency to protrude toward a side of the locking sleeve facing away from the second component.

2. The needle clamping device according to claim 1, wherein the first end of the inner shaft is provided with a first radial hole in a radial direction, a hole wall portion of the first radial hole facing away from an end surface of the first end is the first limiting surface, the locking sleeve is provided with a second radial hole in the radial direction, a hole wall portion of the second radial hole which has the same direction as the end surface of the first end of the inner shaft is the second limiting surface, and the first limiting surface and the second limiting surface are arranged diagonally opposite to each other.

3. The needle clamping device according to claim 2, wherein the first end of the inner shaft is located in the locking sleeve, and a limiting rod is arranged in the locking sleeve.

4. The needle clamping device according to claim 1, wherein the first end of the inner shaft is provided with a flange protruding along the radial direction, the flange is located on a side portion of an end of the locking sleeve facing away from the second component, a gap is formed between the flange and the end of the locking sleeve facing away from the second component, a side surface of the flange facing the locking sleeve is the first limiting surface, and an end surface of the first end facing the flange is the second limiting surface.

5. The needle clamping device according to claim 1, wherein the handle member comprises a cylinder portion and a handle portion, the cylinder portion is connected with the handle portion, the handle portion protrudes radially out of the cylinder portion, the cylinder portion and the handle portion are sleeved outside the second end of the inner shaft, and are threadedly connected with the second end of the inner shaft, an end of the handle portion is contacted with the second end portion of the first clamping arm, and when the handle portion is rotated, the handle portion can drive the inner shaft to move in the axial direction, and drive the locking sleeve to squeeze the second end portion of the second clamping arm.

6. The needle clamping device according to claim 1, wherein the handle member is a cam handle, the cam handle comprises a cam portion and a handle portion, the cam portion is connected with the handle portion, the cam portion is rotatably connected to the second end of the inner shaft, and when the handle portion rotates to drive the cam portion to rotate, the handle portion can drive the inner shaft to move in the axial direction and drive the locking sleeve to squeeze the second end portion of the second clamping arm.

7. The needle clamping device according to claim 1, wherein the inner shaft is connected to the locking sleeve in a manner of circumferential limit.

8. The needle clamping device according to claim 7, wherein an outer peripheral surface of the inner shaft comprises at least a plane area parallel to the inner shaft, an inner peripheral surface of the through hole of the locking sleeve is provided with a matching surface matched with the plane area, the matching surface is fitted with the plane area to form the circumferential limit.

9. A leg support device comprising a needle clamping device of claim 1, wherein the leg support device further comprises:
   a base;
   a support rod assembly connected to the base;
   the needle clamping device is arranged on an upper portion of the support rod assembly.

10. The leg support device according to claim 9, wherein the support rod assembly comprises a first support rod assembly and a second support rod assembly respectively disposed on two sides of the base, and at least one of the first support rod assembly and the second support rod assembly is detachably connected to the base.

11. The leg support device according to claim 9, wherein the position of the support rod assembly and the base relative to each other along a length direction of a side of the base is adjustable.

* * * * *